United States Patent
Bruestle

(10) Patent No.: US 9,489,414 B2
(45) Date of Patent: Nov. 8, 2016

(54) PREFIX BURROWS-WHEELER TRANSFORMATIONS FOR CREATING AND SEARCHING A MERGED LEXEME SET

(71) Applicant: Spiral Genetics, Inc., Seattle, WA (US)

(72) Inventor: Jeremy Bruestle, Seattle, WA (US)

(73) Assignee: Spiral Genetics, Inc., Seattle, WA (US)

( * ) Notice: Subject to any disclaimer, the term of this patent is extended or adjusted under 35 U.S.C. 154(b) by 209 days.

(21) Appl. No.: 14/292,787

(22) Filed: May 30, 2014

(65) Prior Publication Data

US 2015/0347088 A1    Dec. 3, 2015

(51) Int. Cl.
*G06F 17/30* (2006.01)
*G06F 19/22* (2011.01)

(52) U.S. Cl.
CPC ......... *G06F 17/30339* (2013.01); *G06F 19/22* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,770,860 | A * | 6/1998 | Franzen | H01J 49/0418 250/288 |
| 7,599,802 | B2 * | 10/2009 | Harwood | G06Q 50/22 463/30 |
| 2009/0270277 | A1 * | 10/2009 | Glick | G06F 19/22 506/24 |
| 2012/0209625 | A1 * | 8/2012 | Armstrong | G06F 19/326 705/3 |
| 2012/0310990 | A1 * | 12/2012 | Viegas | G06F 17/30058 707/794 |
| 2012/0330567 | A1 * | 12/2012 | Bauer | G06F 19/22 702/20 |

* cited by examiner

*Primary Examiner* — Etienne Leroux
(74) *Attorney, Agent, or Firm* — Han Santos Reich, PLLC

(57) ABSTRACT

Systems and methods to create a merged lexeme set from a first lexeme set and a second lexeme set such that an existential lexeme search may be performed on both data originally from the first lexeme set and data originally from the second lexeme set via the merged lexeme set, and wherein information in the merged lexeme set includes information as to which lexeme set a lexeme originated. Specifically Prefix Burrows-Wheeler Transform ("PBWT") systems and techniques are applied to the scenario where a plurality lexeme sets are merged to a single merged lexeme set. Additionally, applications of PBWT systems and techniques as applied to genome sequence data and k-Mer searches are disclosed.

25 Claims, 12 Drawing Sheets

| Figure 3a |
|---|
| ACTG |
| CTGC |
| CCGC |
| ATGC |
| 300a |

| Figure 3b |
|---|
| ACTG |
| CTG |
| TG |
| G |
| CTGC |
| TGC |
| GC |
| C |
| CCGC |
| CGC |
| GC |
| C |
| ATGC |
| TGC |
| GC |
| C |
| 300b |

| Figure 3c |
|---|
| ACTG |
| ATGC |
| C |
| C |
| C |
| CCGC |
| CGC |
| CTG |
| CTGC |
| G |
| GC |
| GC |
| GC |
| TG |
| TGC |
| TGC |
| 300c |

| Figure 3d |
|---|
| ACTG |
| ATGC |
| CCGC |
| CGC |
| CTGC |
| GC |
| TGC |
| 300d |

| Figure 3e | |
|---|---|
| ACTG$ | |
| CTG/A | |
| ATGC$ | |
| TGC/A | |
| CCGC$ | |
| CGC/C | |
| CGC$ | |
| GC/C | |
| CTGC$ | |
| TGC/C | |
| GC$ | |
| C/G | |
| TGC$ | |
| GC/T | |
| 300e | |

| Figure 3f | |
|---|---|
| ACTG$ | |
| ATGC$ | |
| C/G | |
| CCGC$ | |
| CGC/C | |
| CGC$ | |
| CTG/A | |
| CTGC$ | |
| GC/C | |
| GC/T | |
| GC$ | |
| TGC/A | |
| TGC/C | |
| TGC$ | |
| 300f | |

| Figure 3g | |
|---|---|
| ACTG$ | |
| ATGC$ | |
| C/G | |
| CCGC$ | G |
| CGC/C | |
| CGC$ | C |
| CTG/A | |
| CTGC$ | A |
| GC/C | |
| GC/T | |
| GC$ | C,T |
| TGC/A | |
| TGC/C | |
| TGC$ | A,C |
| 300g | |

| Figure 3h | |
|---|---|
| ACTG | |
| ATGC | |
| CCGC | G |
| CGC | C |
| CTGC | A |
| GC | C,T |
| TGC | A,C |
| 300h | |

| Figure 3i | | | |
|---|---|---|---|
| 0: | ACTG | | 4 |
| 1: | ATGC | | 4 |
| 2: | CCGC | G | 4 |
| 3: | CGC | C | 3 |
| 4: | CTGC | A | 4 |
| 5: | GC | C,T | 2 |
| 6: | TGC | A,C | 3 |
| 300i | | | |

| Figure 3j | | | | | | | |
|---|---|---|---|---|---|---|---|
| | | | | A | C | G | T |
| 0: | ACTG | | 4 | 0 | 0 | 0 | 0 |
| 1: | ATGC | | 4 | 0 | 0 | 0 | 0 |
| 2: | CCGC | G | 4 | 0 | 0 | 0 | 0 |
| 3: | CGC | C | 3 | 0 | 0 | 1 | 0 |
| 4: | CTGC | A | 4 | 0 | 1 | 1 | 0 |
| 5: | GC | C,T | 2 | 1 | 1 | 1 | 0 |
| 6: | TGC | A,C | 3 | 1 | 2 | 1 | 1 |
| 7: | | | | 2 | 3 | 1 | 1 |
| 300j | | | | | | | |

| Figure 3k |
|---|
| A: 0 |
| C: 2 |
| G: 5 |
| T: 6 |
| 300k |

400

| 402 Lexeme | 404 Length | 406 Prefixes | 408 (Prefix Counts) A | C | G | T |
|---|---|---|---|---|---|---|
| CGC not coded | 3 0000011 | C 0100 | 0 not | 0 coded | 1 | 0 |
| CTGC not coded | 4 0000100 | A 1000 | 0 not | 1 coded | 1 | 0 |

|      |      |     | A | C | G | T |
|------|------|-----|---|---|---|---|
| 0:   | ACTG |     | 4 | 0 | 0 | 0 | 0 |
| 1:   | ATGC |     | 4 | 0 | 0 | 0 | 0 |
| 2:   | CCGC | G   | 4 | 0 | 0 | 0 | 0 |
| 3:   | CGC  | C   | 3 | 0 | 0 | 1 | 0 |
| 4:   | CTGC | A   | 4 | 0 | 1 | 1 | 0 |
| 5:   | GC   | C,T | 2 | 1 | 1 | 1 | 0 |
| 6:   | TGC  | A,C | 3 | 1 | 2 | 1 | 1 |
| 7:   |      |     |   | 2 | 3 | 1 | 1 |

Initialize X to first record
Initialize Y to dummy record
[0, 7)

|      |      |     | A | C | G | T |
|------|------|-----|---|---|---|---|
| 0:   | ACTG |     | 4 | 0 | 0 | 0 | 0 |
| 1:   | ATGC |     | 4 | 0 | 0 | 0 | 0 |
| 2:   | CCGC | G   | 4 | 0 | 0 | 0 | 0 |
| 3:   | CGC  | C   | 3 | 0 | 0 | 1 | 0 |
| 4:   | CTGC | A   | 4 | 0 | 1 | 1 | 0 |
| 5:   | GC   | C,T | 2 | 1 | 1 | 1 | 0 |
| 6:   | TGC  | A,C | 3 | 1 | 2 | 1 | 1 |
| 7:   |      |     |   | 2 | 3 | 1 | 1 |

X = 0 + 2 no increment since 4 >= 1
Y = 3 + 2
[2, 5)

|      |      |     | A | C | G | T |
|------|------|-----|---|---|---|---|
| 0:   | ACTG |     | 4 | 0 | 0 | 0 | 0 |
| 1:   | ATGC |     | 4 | 0 | 0 | 0 | 0 |
| 2:   | CCGC | G   | 4 | 0 | 0 | 0 | 0 |
| 3:   | CGC  | C   | 3 | 0 | 0 | 1 | 0 |
| 4:   | CTGC | A   | 4 | 0 | 1 | 1 | 0 |
| 5:   | GC   | C,T | 2 | 1 | 1 | 1 | 0 |
| 6:   | TGC  | A,C | 3 | 1 | 2 | 1 | 1 |
| 7:   |      |     |   | 2 | 3 | 1 | 1 |

X = 0 + 5 no increment since 2 >= 2
Y = 1 + 5
[5, 6)

|      |      |     | A | C | G | T |
|------|------|-----|---|---|---|---|
| 0:   | ACTG |     | 4 | 0 | 0 | 0 | 0 |
| 1:   | ATGC |     | 4 | 0 | 0 | 0 | 0 |
| 2:   | CCGC | G   | 4 | 0 | 0 | 0 | 0 |
| 3:   | CGC  | C   | 3 | 0 | 0 | 1 | 0 |
| 4:   | CTGC | A   | 4 | 0 | 1 | 1 | 0 |
| 5:   | GC   | C,T | 2 | 1 | 1 | 1 | 0 |
| 6:   | TGC  | A,C | 3 | 1 | 2 | 1 | 1 |
| 7:   |      |     |   | 2 | 3 | 1 | 1 |

X = 0 + 6 no increment since 3 >= 3
Y = 1 + 6
[6, 7)

|      |      |     | A | C | G | T |
|------|------|-----|---|---|---|---|
| 0:   | ACTG |     | 4 | 0 | 0 | 0 | 0 |
| 1:   | ATGC |     | 4 | 0 | 0 | 0 | 0 |
| 2:   | CCGC | G   | 4 | 0 | 0 | 0 | 0 |
| 3:   | CGC  | C   | 3 | 0 | 0 | 1 | 0 |
| 4:   | CTGC | A   | 4 | 0 | 1 | 1 | 0 |
| 5:   | GC   | C,T | 2 | 1 | 1 | 1 | 0 |
| 6:   | TGC  | A,C | 3 | 1 | 2 | 1 | 1 |
| 7:   |      |     |   | 2 | 3 | 1 | 1 |

X = 1 + 5 and incremented since 4 > 3
Y = 1 + 5
[7, 6)

| List 1 | List 2 |
| --- | --- |
| ACCG | ACTG |
| CTGC | CTGC |
| CCCC | CCGC |
| ATGC | ATGC |

| List 1 | List 2 |
| --- | --- |
| ACCG | ACTG |
| CCG | CTG |
| CG | TG |
| G | G |
| CTGC | CTGC |
| TGC | TGC |
| GC | GC |
| C | C |
| CCCC | CCGC |
| CCC | CGC |
| CC | GC |
| C | C |
| ATGC | ATGC |
| TGC | TGC |
| GC | GC |
| C | C |

| List 1 | List 2 |
| --- | --- |
| ACCG | ACTG |
| ATGC | ATGC |
| C | C |
| C | C |
| C | C |
| CC | CCGC |
| CCC | CGC |
| CCCC | CTG |
| CCG | CTGC |
| CG | G |
| CTGC | GC |
| G | GC |
| GC | GC |
| GC | TG |
| TGC | TGC |
| TGC | TGC |

| List 1 | List 2 |
| --- | --- |
| ACCG | ACTG |
| ATGC | ATGC |
| CCCC | CCGC |
| CCG | CGC |
| CG | CTGC |
| GC | GC |
| TGC | TGC |

| List 1 |   | List 2 |   |
| --- | --- | --- | --- |
| ACCG | 1 | ACTG | 2 |
| ATGC | 1 | ATGC | 2 |
| CCCC | 1 | CCGC | 2 |
| CCG | 1 | CGC | 2 |
| CG | 1 | CTGC | 2 |
| GC | 1 | GC | 2 |
| TGC | 1 | TGC | 2 |

| ACCG | 1 |
| --- | --- |
| ACTG | 2 |
| ATGC | 1 |
| ATGC | 2 |
| CCCC | 1 |
| CCG | 1 |
| CCGC | 2 |
| CG | 1 |
| CGC | 2 |
| CTGC | 2 |
| GC | 1 |
| GC | 2 |
| TGC | 1 |
| TGC | 2 |

| Seq | List | Orig 1 | Orig 2 | 1st Char Overlap |
| --- | --- | --- | --- | --- |
| ACCG | 1 | 0 | 0 | 0 |
| ACTG | 2 | 1 | 0 | 2 |
| ATGC | 1 | 1 | 1 | 1 |
| ATGC | 2 | 2 | 1 | 4 |
| CCCC | 1 | 2 | 2 | 0 |
| CCG | 1 | 3 | 2 | 2 |
| CCGC | 2 | 3 | 2 | 3 |
| CG | 1 | 3 | 3 | 1 |
| CGC | 2 | 4 | 3 | 2 |
| CTGC | 2 | 4 | 4 | 1 |
| GC | 1 | 4 | 4 | 0 |
| GC | 2 | 5 | 4 | 2 |
| TGC | 1 | 5 | 5 | 0 |
| TGC | 2 | 6 | 5 | 3 |
| - | - | 6 | 6 | - |

| List | Orig 1 | Orig 2 | 1st Char Overlap |
| --- | --- | --- | --- |
| 1 | 0 | 0 | 0 |
| 2 | 1 | 0 | 2 |
| 1 | 1 | 1 | 1 |
| 2 | 2 | 1 | 4 |
| 1 | 2 | 2 | 0 |
| 1 | 3 | 2 | 2 |
| 2 | 3 | 2 | 3 |
| 1 | 3 | 3 | 1 |
| 2 | 4 | 3 | 2 |
| 2 | 4 | 4 | 1 |
| 1 | 4 | 4 | 0 |
| 2 | 5 | 4 | 2 |
| 1 | 5 | 5 | 0 |
| 2 | 6 | 5 | 3 |
| - | 6 | 6 | - |

| Row | Seq  | List | Orig 1 | Orig 2 | 1st Char Overlap |
|-----|------|------|--------|--------|------------------|
| 0   | ACCG | 1    | 0      | 0      | 0                |
| 1   | ACTG | 2    | 1      | 0      | 2                |
| 2   | ATGC | 1    | 1      | 1      | 1                |
| 3   | ATGC | 2    | 2      | 1      | 4                |
| 4   | CCCC | 1    | 2      | 2      | 0                |
| 5   | CCG  | 1    | 3      | 2      | 2                |
| 6   | CCGC | 2    | 3      | 2      | 3                |
| 7   | CG   | 1    | 3      | 3      | 1                |
| 8   | CGC  | 2    | 4      | 3      | 2                |
| 9   | CTGC | 2    | 4      | 4      | 1                |
| 10  | GC   | 1    | 4      | 4      | 0                |
| 11  | GC   | 2    | 5      | 4      | 2                |
| 12  | TGC  | 1    | 5      | 5      | 0                |
| 13  | TGC  | 2    | 6      | 5      | 3                |
| 14  | -    | -    | 6      | 6      | -                |

1100

PREFIX BURROWS-WHEELER TRANSFORMATIONS FOR CREATING AND SEARCHING A MERGED LEXEME SET

BACKGROUND

When performing data processing, a computer is used to take data, which may be represented as a structure in a computer memory and/or a file format on a persistent computer memory, and to perform operations, called data operation, on the data. Data operations are typically performed on data is typically demarcated into discrete sets, called data sets. Typical data operations on data sets in the course of data processing may include searching, which is retrieval a desired subset of a data set; sorting, which is re-organizing the data set; and transformation which is converting the data set from one representation to another.

Over time processing power available for data processing has increased rapidly, but in many cases the amount of data applied to data processing techniques has increased even more rapidly. Accordingly, data processing is in need of improved searching, sorting, transformation, and other data operations.

Data operations are generally improved either by reducing the amount of working memory used to perform the operation, or by improving the processing efficiency of the operation as to reduce processing time. In most cases, the amount of working memory and processing efficiency results in an optimization tradeoff. Reducing the amount of working memory in an operation often results in lower processing efficiency. Conversely, increasing processing efficiency results in a larger amount of memory used during processing. It is relatively rare to achieve reduced memory utilization and greater processing efficiency in the same optimization.

Nonetheless, for large data sets, which are data sets so large that performing data operations are too slow to enable interactive processing, improving processing efficiency at the expense of memory utilization may render the optimization impractical. Increasing the size of a very large data set may result in the amount of memory utilized to be larger than the amount of memory available. Accordingly, even if an optimization for a data operation's processing improvement is significant, it may not be available for implementation because of the amount of available is insufficient. Thus many optimization techniques are impractical for large data set applications.

Presently there are many large data set applications. Some examples include, document processing, image processing, multimedia processing and bioinformatics. For example, in the case of bioinformatics, the data processed is comprised of genetic information which define an organism. Genetic information is comprised of a series of base pairs adenine-thymine and guanine-cytosine. The more complex the organism, the more base pairs are used to defined the organism. For example, the *Escherichia Coli* bacterium uses approximately 4.6 million base pairs. In contrast, simple viruses may use as little as a few thousand base pairs.

A major application of bioinformatics is in the analysis of genetic conditions in human beings, in the search for medical therapies. The genetic information for a human being is 3.2 billion base pairs. Accordingly, every byte allocated to a base pair in an effort to improve processing, potentially adds an additional 3.2 Gb of working memory. When performing sequence comparisons, with different instances of human beings or other organisms under analysis, the amount of memory used during data processing may rapidly expand to an unmanageable amount.

Accordingly, there is a need for techniques to improve processing speed of data operations on large data sets, such as in bioinformatics, while reducing the amount of memory used.

BRIEF DESCRIPTION OF THE DRAWINGS

The Detailed Description is set forth with reference to the accompanying figures.

FIGS. 3$a$, 3$b$, 3$c$, 3$d$, 3$e$, 3$f$, 3$g$, 3$h$, 3$i$, 3$j$ and 3$k$ are illustrations of an exemplary data set undergoing a Prefix Burrows-Wheeler Transform.

FIG. 4 is an exemplary compressed data memory layout for a prefix table in a Prefix Burrows-Wheeler Transform.

FIGS. 6$a$, 6$b$, 6$c$, 6$d$ and 6$e$ are illustrations of exemplary data transformed by a Prefix Burrows-Wheeler Transform being traversed via an exemplary k-Mer search.

FIGS. 9$a$, 9$b$, 9$c$, 9$d$, 9$e$, 9$f$, 9$g$ and 9$h$ are illustrations of exemplary data transformed by a process to create a merged lexeme set using Prefix Burrows-Wheeler Transform techniques.

FIG. 11 is an illustration of an exemplary merged lexeme set being searched using Prefix Burrows-Wheeler Transform techniques.

DETAILED DESCRIPTION

Figure 1:
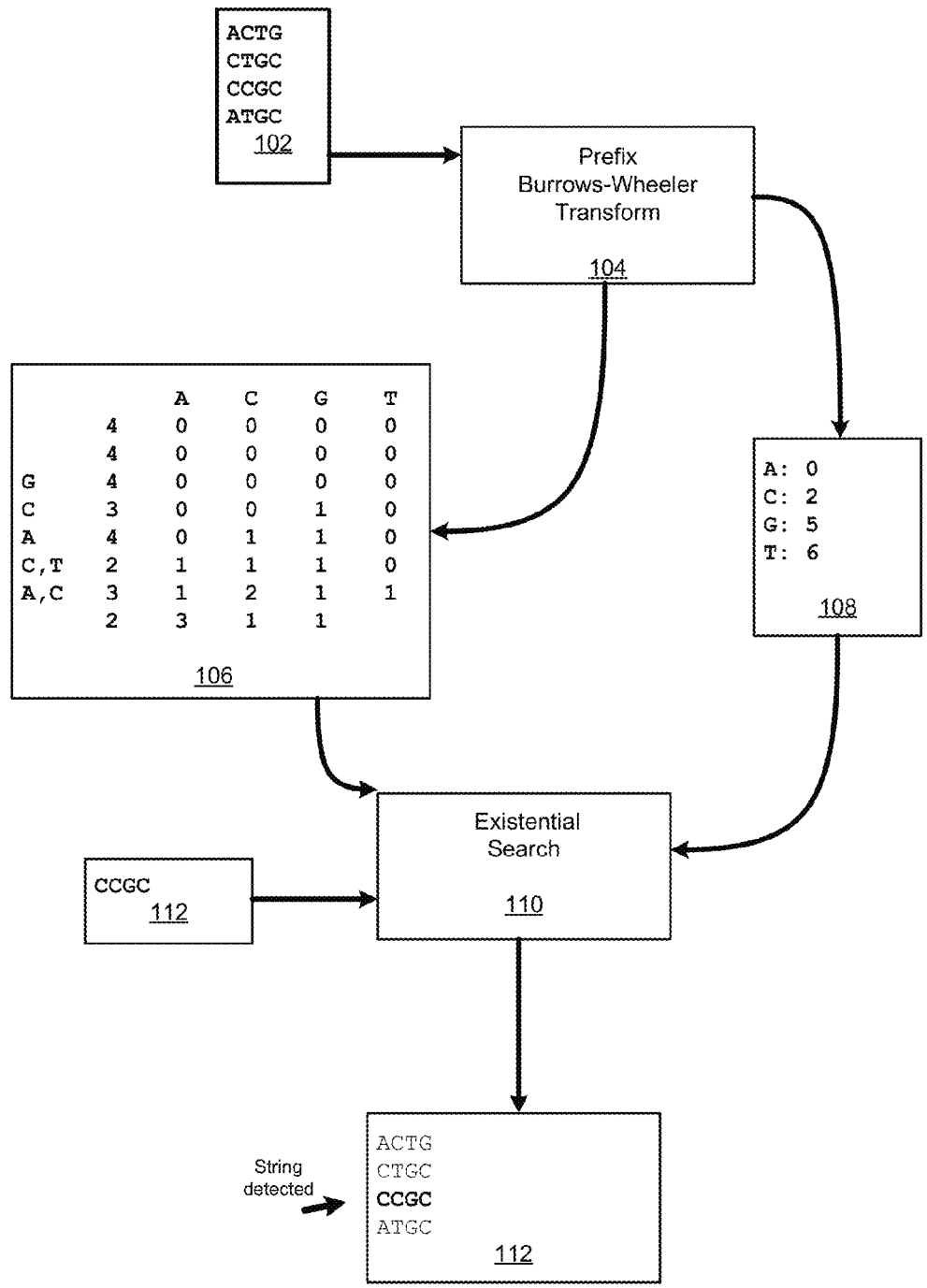
FIG. 1 is a top level diagram of a Prefix Burrows-Wheeler Transform.

Context of Prefix Burrows-Wheeler Transform Techniques
Overview

Systems and methods to perform data operations on large data sets optimized for both performance time and memory are disclosed herein. Specifically, Prefix Burrows-Wheeler Transform ("PBWT") techniques are disclosed. In order to aid disclosure, this section describes underlying PBWT.
Closed Domains of Data and Data Representation Optimizing data operations may take advantage of insight into the data populating a data set. Specifically, the set of all possible data that may populate a data set is called the domain of a data set. Some domains are open, where any datum may be included in the data set. An example of an open domain is a representation of analogue signal data where the frequency and amplitude of the signal that may be represented is not initially restricted. Other domains are closed where only a limited set of data may be admitted into a data set. An example of a closed domain is text data where the only data admitted are text characters. In some systems, text characters are limited to American Standard Code for Information Interchange ("ASCII") characters, a predefined set of 128 characters representing Latin alphanumeric characters, punctuation marks and common formatting characters. Accordingly each ASCII character could be represented in seven bits of information (i.e., $2^7$=128). There are other closed domains comprised of 256 alphanumeric characters which may include the Extended Binary Coded Decimal Interchange Code ("EBCDIC") character set and the IBM Extended ASCII character set, both of which have characters represented by eight bits of information (i.e., $2^8$=256).

Note that a closed domain need not be comprised of an entire alphabet for a natural language. As previously mentioned, genetic base pairs are comprised of adenine-thymine and guanine-cytosine pairs. Accordingly, a data domain for genetic information may be the closed set of adenine, thymine, guanine and cytosine, commonly denoted A, T, G and C. As there are only four elements in this closed domain, these elements may be represented in two bits (i.e., $2^2$=4).

Understanding the domain of a data set and understanding how that domain is represented in a computer memory, may aid in identifying efficiencies in data operations. For example, consider the example where a computer program works with ASCII characters comprised solely of uppercase and lowercase alphabetic characters, i.e., no numbers, punctuation, or formatting characters. The uppercase letter 'A' is represented by the number 65 (or 0b1000001 in binary), and the lowercase letter 'a' is represented by the number 97 (or 0b1100001 in binary). Note that the lowercase character has a value of 32 more than the uppercase character. Thus toggling the sixth bit correspondingly toggles the character between uppercase and lowercase letters.

A computer program to convert lowercase letters all into uppercase letters in ASCII might have been implemented by a routine that tested each character as to whether it was a lowercase or uppercase character. If the character was a lowercase letter, the program might have invoked a lookup table to convert the lowercase letter into its corresponding uppercase character.

However, a much more efficient and equivalent program could be implemented making use of the knowledge of how ASCII uppercase and lowercase characters are coded, and simply have applied an exclusive-or bitmask of (0b0100000) to each character. Thus, no memory would have been used for the lookup table, and a single operation (the exclusive-or) need have been used per character rather than the two operations of testing for case and for replacing. Accordingly, this implementation represents both an improvement in the amount of working memory used and increase in processing efficiency at the same time.

Search Techniques and Optimization

In the foregoing discussion, we've described how insight as to how a data set is represented in memory may be used to optimize a data operation. Insight as to what specific data operation is to be performed may also be used to optimize implementation of that data operation. For example, searching is a common data operation where a pattern is detected in a data set. However, search data operations have different degrees of fidelity.

A search data operation may be existential, where the search data operation simply determines whether the pattern exists in the data set or not. For example an existential search for the letter 'C' in data set "ABBBCCCD" might simply return the value "TRUE" since the letter 'C' was indeed in the data set.

A search data operation may be cardinal, where the search data operation not only tests for existence, but also counts the number of instances of the pattern to be detected. For example, a cardinal search for the letter 'C' in data set "ABBBCCCD" might return 3, since the letter 'C' appeared three times in the data set.

A search operation may be positional, where the search data operation returns the position of the pattern to be detected. For example, a positional search for the letter 'C' in data set "ABBBCCCD" might return 5, since the first instance of the letter 'C' in the data set was in the fifth position.

Thus if it was understood that a computer program was to be optimized for existential search, rather than cardinal search, an implementation might be to scan a data set until it found the first instance of the pattern to be detected. This contrasts to a cardinal search which might scan the entire data set as it counted the number of instances of the pattern to be detected. Thus a data set comprised of the letter 'C' followed by a million 'A' characters searching for the letter 'C' would terminate at the first character if it were an existential search, whereas a cardinal search would be obliged to scan the subsequent million 'A' characters with no guarantee of finding another 'C' character. This is an example of how, understanding the fidelity of a data operation may be used to optimize implementation of that data operation.

Transformations of Data Representation

As shown above, information how a data set is represented in memory may be used to optimize the implementation of a data operation. However, a computer program may not receive data in an optimized format for a data operation. Data as it arrives in its original data representation, often called "raw data", may be converted into an alternative data representation which is optimized for a particular data operation. This conversion is called a transformation.

Transformations come in many forms. Transformations may order data according to predetermined conventions. Such transformations are called "sorting" data operations. Other transformation may reduce the size of the data representation. Such transformations are called "compression" data operations. Yet other transformation may generate lookup tables and/or indices to aid in the performance of a data operation. The following subsections will discuss these and other transformations.

A transformation is in itself a data operation and accordingly may be optimized. However, typically transformations convert data into a data representation optimized for a particular data operation. The converted data is persisted in a persistent memory device called a "data format", or "format" for short. Since the particular data operation typically operates only on the optimized data format, a transforming data is sometimes called "preprocessing data." Specifically, the processing used to transform the data is persisted in the data format, so that the processing need not be repeated every time the particular data operation is performed. Thus preprocessing is in of itself a way to optimize the particular data operation.

As stated above, for large data sets (as well as in other contexts), the desired result is to reduce both the working memory used in implementing a particular data operation, and to increase the processing efficiency. One route would then be to perform a data transformation that performs both a compression and creates a data representation optimized for a particular data operation.

Lexicographical Sorting

A common data operation is to perform a sort, which is to order data in a data set according to predetermined convention. Sorting is a transformation which generally optimizes searching Specifically, when a data set is in a particular order, a computer program scanning the data set can make determine where a pattern to be detected is likely to be. Binary search and B-Tree searches are well-known examples of search algorithms that rely on sorted data.

A lexicographical sort is a sort where the predetermined convention used to order the data set is to posit an order on the characters comprising a closed data domain of the data set. The data in the data set is comprised of sequences of characters, called "lexemes". A lexeme made up of alphanumeric characters is also called a "string." The set of lexemes in the data set is called a "lexicon". Lexemes that are lexicographically sorted are sorted according to the order and the places of the characters in the lexeme.

A common application of a lexicographical sort is to perform an alphabetical sort on strings. The letters of the alphabet have a posited order, where each letter is known to precede or succeed another letter. In English, letters are generally read from left to right. Thus a letter placed to the left of another letter in a string takes precedence in ordering the string with respect to other strings. Accordingly, "do" precedes "hi" because 'd' precedes 'h' in alphabetical order. Although 'o' succeeds 'I' in alphabetical order, the leftmost characters in the string have precedence when performing an alphabetical sort.

Compression Techniques

A transformation that reduces the size of a data representation in computer memory is a compression data operation. Transformations may be "lossy" where information with respect to a particular data operation is lost via the transformation. Transformations may be lossless where information with respect to a particular data operation is preserved during the transformation.

One example of compression is run length encoding. Consider the data set comprised of the 12 characters, "AAABBBBCCCCCBBB". The data set might be represented in 6 characters "3A4B5C3B" meaning that there are "three A's, four B's, five C's followed by three B's." Note that the amount of memory used to represent the data set has effectively been reduced, i.e., the data set has been compressed.

Now consider the same data set compressed as "3A7B5C". Specifically, the information about the run of four B's and the run of three B's has been combined. With respect to an existential search and a cardinal search, the transformation has been lossless. Specifically, both an existential search and a cardinal search are able to provide an accurate result with the new compressed data operation without loss of information. However, with respect to a positional search, the transformation has been lossy. While the positional search could determine that the letter 'B' was in the dataset, it could not determine whether there was B in the last position or any other position. As this positional information has been lost, the transformation has been lossy with respect to a positional search.

Note that whether a transformation is lossy or lossless is with respect to a specific data operation. From the perspective of the existential and cardinal searches, those data operations not only are able to provide the correct result, they are also able to provide the correct result faster. Thus this data transformation may be said to be optimized for existential and cardinal searches. Such tradeoffs are common in design optimizations for data representations. For example, many database formats tradeoff performance for record insert data operations in exchange for fast read/search data operations.

Lookups/Indexing

Data operations may be optimized by utilizing supplementary data structures that contain information on how to perform an operation and/or information on the layout of a data representation. Such supplementary data structures are called "lookups". If a lookup is in the form of a set of tuples, then the lookup is called a "lookup table." If the lookup stores positional information of data in the data representation, then the lookup is called an "index."

An example of a lookup is used in Huffman encoding compression. Characters in a textual data set are analyzed for frequency. A lookup is generated that maps each character used in the textual data set with a prefix-free code, which is a bit string where each string is guaranteed never to be the prefix of another bit string. More frequent characters are mapped in the lookup to shorter prefix codes. Then the textual data set is transformed by replacing each instance of a character with its respective prefix code per the lookup.

The lookup in a Huffman encoding is typically in the form of a tree. However, it may also be represented as a table. Also note that whenever the Huffman encoded data set is transferred, so too is the lookup. In this way, a recipient may decode the Huffman encoded data set.

Turning to indexes, consider the 12 character string "AAABBBBCCCCC". If a programmer were to optimize positional search data operations, and also knew that the data set was guaranteed to be in order, the programmer might prepare an index with three records as follows: "A, 1"; "B, 4"; and "C, 8". Thus in order to find the location of the first 'B' in the dataset, instead of scanning the characters in the dataset, the positional search data operation need only look up the position in the index resulting in faster data processing. Note that generating the index in the first place might have made use of a full scan of the characters in the dataset. However, by generating and storing the index during preprocessing, the index provides an optimization that may be realized whether a positional search data operation is performed.

Merged Sets and Search Operations

Data operations may include operations that involve a plurality of datasets. A search data operation, such as an existential search for a search pattern may be performed on a first dataset and thereafter on a second dataset. While the search will find all instances of the search pattern on both the first and second datasets, it may be desirable to merge the first and second datasets. In one case, the motivation may be that the merged first and second datasets, where compression and other techniques are applied, result in a merged dataset smaller than the first and second datasets together. Since the merged dataset is lossless with respect to the search, the savings in working memory does not incur a tradeoff in accuracy.

As described above, lossless transforms are in with respect to a data operation. In some cases, it is desirable to retain (i.e., not lose) the identity of the original dataset for a record in a merged dataset. As will be described below, it is in fact possible to create a merged dataset, lossless with respect to an existential search, which retains the identity of the original dataset for each record in the merged dataset.

Performing a Prefix Burrows-Wheeler Transform

Overview

This section describes how to perform a Prefix Burrows-Wheeler Transform ("PBWT"). PBWT is a novel modification of techniques used in block-sorting compression, such as in a Burrows-Wheeler Transform, to optimize for existential searches in data sets with closed data domains. As will be described in other sections, applications extend beyond bioinformatics. However, for illustrative purposes, the following discussion will use bioinformatics data as an exemplary context to describe PBWT and its associated data operations.

FIG. 1 is a top level diagram 100 of a PBWT and an existential search operation. In the present illustration, bioinformatics sequences are shown as the data to be operated on. Raw data 102 comprised of a data set of lexemes made up of a closed domain of characters is received by a PBWT transformation routine 104. The PBWT transformation routine 104 converts the raw data into a prefix table 106 and an offset table 108. The prefix table 106 provides a lookup to identify all single character prefixes for any substring of a lexeme in the data set. The offset table 108 provides a lookup to identify the offset location of lexemes in the prefix table starting with a given single character. The prefix table 106 and the offset table 108 represent a significant compression of the original raw data.

An existential search routine 110 may search for an arbitrary string 112 of the domain of characters may be performed on the prefix table 106 and offset table 108. The existential search can accordingly determine whether the string 112 exists 114 in the representation. Via PBWT, the existential search may be performed significantly more quickly than prior techniques, without loss of accuracy.

Figure 2:
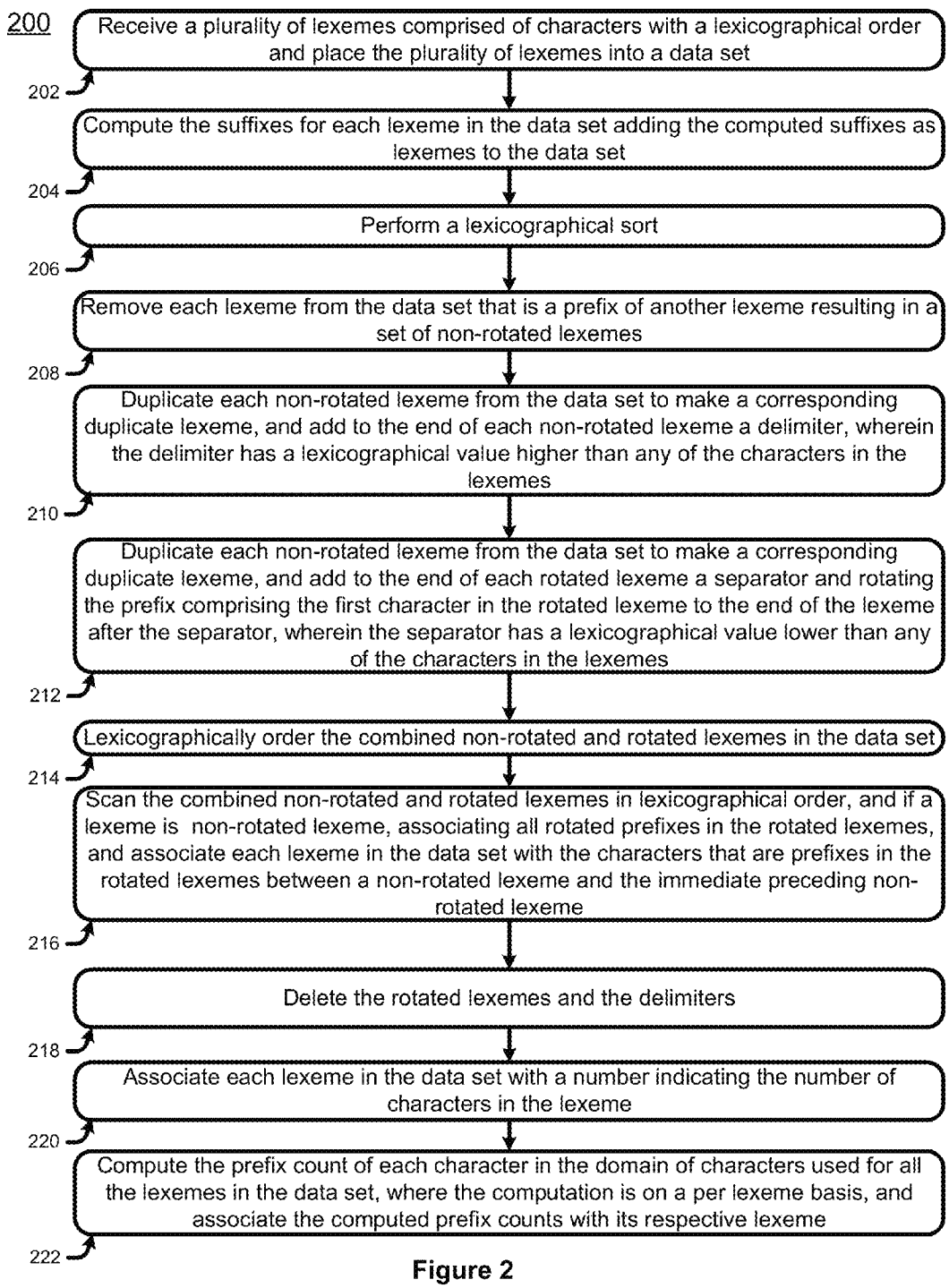
FIG. 2 is a flow chart of an exemplary performance of a Prefix Burrows-Wheeler Transform.

FIG. 2 is a flow chart 200 of an exemplary performance of a PBWT. FIGS. 3a through 3k illustrate different stages 300a-300k in generating a PBWT prefix table and a PBWT offset table in performing a PBWT.

Receive Raw Data

In performing a PBWT, a computing device receives raw data in block 202. The raw data generally arrives in the form of data strings 300a as shown in FIG. 3a. Here, the data strings 300a are four genetic sequences each with four nucleic acids. It is to be stressed that the actual lengths of the sequences can vary, and the data set domain may be any closed domain where the characters comprising the domain have a posited order, lending themselves to a lexicographical sort.

Generate Suffixes for Each Sequence

Once raw data is received, the received data will be analyzed and subjected to character rotation techniques to identify all prefixes. The identity and location of the prefixes will be used to generate a prefix table. In block 204 of FIG. 2, the suffixes for each sequence is generated and added to the data set. The result 300b is shown in FIG. 3b. For example, the sequence ACTG has a suffix of CTG, of TG and of G.

Perform a Lexicographical Sort and Remove Prefix Matches

Now that the data set includes all suffixes, in block 206 of FIG. 2, the data set is lexicographically sorted. The result 300c of the lexicographical sort is shown in FIG. 3c.

While the lexicographical sort 206 is used to guarantee the lexicographical order of the lexemes in the data set, it also aids in removing lexemes that are prefix matches as in block 208 of FIG. 2. Specifically, in one embodiment, the sorted data set may be linearly scanned. If a lexeme is identical to or is a prefix of the immediately succeeding lexeme, then it is a prefix match and is removed. For example the suffix GC for ATGC is identical to the suffix GC for CCGC, and thus the duplicate is removed. Similarly, the suffix TG is a prefix of TGC and is also removed. The result 300d of the removed prefix matches is shown in FIG. 3d.

Further note that due to the initial lexicographical sort 206, the result 300d with the prefix matches removed is also lexicographically sorted.

Perform a First Letter Rotation

The data set will now be subjected to letter rotation techniques in order to determine the location of relative prefixes. In block 210 of FIG. 2, each lexeme is duplicated and delimiter is added to the end of each original lexeme. Note that the delimiter is a member of the closed data domain, but is lexicographically ordered after all the elements in the lexemes. This is done so that the lexicographical order of the lexemes is the same with the delimiter as it is without the delimiter.

In block 212 of FIG. 2, each new duplicate lexeme has its first letter rotated to the end of the lexeme and separated by a separator character. The separator is also a member of the closed data domain, but is lexicographically order before all the elements in the lexemes. Again, this is done so that the lexicographical order of the rotated lexeme is the same with the separator as it is without the separator.

The result 300e of the duplication, first letter rotation, and the addition of the delimiter and separator is shown in FIG. 3e. In this Figure, the delimiter is the '$' character and the separator is the '/' character.

Lexicographically Sort the Delimited Original and Rotated Lexemes

In block 214 of FIG. 2, the delimited/rotated/separated lexemes are lexicographically sorted together. Once this sort is performed, the data is in condition to generate a PBWT prefix table. The result of the lexicographical sort 300f is shown in FIG. 3f.

Generate a Non-Rotated and Prefix Paired Lookup Table

The lexicographically sorted data 300f is then scanned in block 216 of FIG. 2 to generate prefix pairs. Specifically, the table is scanned lexeme by lexeme in lexicographical order. The lexeme is first tested to determine whether it is a rotated or non-rotated lexeme. This may be readily ascertained by detecting a delimiter. If there is a delimiter, it is a non-rotated lexeme. Otherwise, it is not.

A non-rotated lexeme is then associated with all rotated characters between itself and the previous non-rotated lexeme. For example, in 300f, CCGC$ will be associated with 'G' because it is the sole rotated character between CCGC$ and the previous non-rotated lexeme ATGC$. Similarly, in 300f, TGC$ will be associated with both 'A' and 'C' since those two characters are the rotated characters between TGC$ and the previous non-rotated lexeme GC$. The rotated characters may be readily extracted by virtue of detecting the separator character. The result 300g of the prefix associations is shown in FIG. 3g.

Once the prefixes have been associated with their respective non-rotated lexemes, the rotated duplicates may be removed and the delimiters removed as in block 218 of FIG. 2. The result 300h of the removals is shown in FIG. 3h.

As can be seen, the rotated characters are the single character prefixes. Because of the rotation 212 and subsequent lexicographical sort 214, the suffix of rotated character will precede the non-rotated lexeme that is a suffix of the rotated character. This is why single character prefixes will immediately precede a non-rotated lexeme.

Add Lexeme Lengths to Finalize Prefix Table Generation

To complete the prefix table, the length of each lexeme remaining in the data set is computed, and associated with that lexeme, as in block 220 of FIG. 2. Specifically, the number of characters in the lexeme is counted. The count may be performed via a linear, sequential scan of the lexeme. Alternatively, the size of the lexeme in memory may be detected and the character count performed by dividing the memory size by a known fixed memory size of each character. For example, in the C programming language, the expression "sizeof(*pLexeme)/sizeof(char);" obtains the memory size a lexeme pointed to by pointer pLexeme and divides it by the size of a character data type. In the case of genetic data, the data may not be represented as characters, but potentially as two-bit values since there are only four nucleic acids. (Note that additional bits may be used in order to include separators and delimiters.)

Regardless of how the length of the lexeme is computed as in 220, the length is then associated with the lexeme. As shown below, this length will be later be compared with patterns being searched for to determine whether a search should be terminated because the lexeme size is smaller than the pattern being searched. The result 300i of the added lexeme lengths is shown in FIG. 3i.

Calculate Prefix Counts

In order to use the prefix table for searches, a prefix count is computed for each character in the closed data domain on a per lexeme basis. This need not be done during preprocessing. Since prefix tables are significantly smaller than their original raw data, it is conceivably practical to compute each session that at least one search is to be performed. However, an implementer may opt to preprocess the prefix table and calculate prefix counts as in block 222 of FIG. 2.

To calculate prefix counts, each lexeme in the data set is associated with a prefix count corresponding each character in the closed data domain that was used in a lexeme in the data set (minus the delimiters and separators). The data set is scanned in lexicographical order. For each lexeme, the counts for each prefix in the previous lexeme are added to the previous prefix counts of the previous lexeme. For example, in prefix count representation 300j in FIG. 3j, the first lexeme is ACTG. Because there are no prefixes in the previous lexeme; indeed there is no previous lexeme to have prefix in the first place, all nucleic acids have a prefix count of 0. This remains true for subsequent lexemes ATCG and CCGC. But note that for CGC, the previous lexeme had prefix of G. Accordingly, the prefix count of G is incremented for lexeme CGC to 1. The next lexeme, CTGC increments the prefix count for C by 1. Since the previous prefix count for G was 1, it too remains at 1 for CTGC. This process is repeated until the last lexeme.

After the last lexeme, a dummy record is added, to take into account any prefixes in the last lexeme. In prefix count representation 300j in FIG. 3j, note the addition of row 7 which shows the total prefix count taking into account the A and C prefixes in the last lexeme TGC. The prefix counts will be used during searches as part of computing existence search bounds for lexemes.

Note that an immediate compression benefit is that the size of a PBWT prefix table is linearly proportional to the number of unique lexemes, rather than the total number of lexemes in a received set of raw lexemes. Unlike prior art techniques, where adding additional redundant lexemes will increase the amount of memory to store the lexeme information, PBWT prefix tables will not increase.

It is to be emphasized that in an existential search data operation, such as a k-Mer search operation describe below, and other related data operations, will only make use of the prefixes, the lengths and the prefix count information. Accordingly, during such data operations, the lexemes need not be stored in memory. Furthermore, the prefix count information may also be compressed or eliminated via rollup techniques. A compressed data layout of a prefix table in memory is described with respect to FIG. 4 below.

Generate an Offset Table

To perform existence searches, with PBWT, a PBWT offset table may also be pre-computed as in block 224 of FIG. 2. The PBWT offset table is a lookup that stores the offset position of the first lexeme in the lexicographically sorted lexemes in the prefix table that start with a particular character in the closed data set. Note that offset positions are not cardinal positions. Offsets denote the amount to add to base number to find a desired data, in this case a particular lexeme. Thus offsets start with 0, whereas cardinal positions start with 1. The associated PBWT offset table 300k for prefix table 300j is shown in FIG. 3k.

As can be seen, the first instance of a lexeme starting with 'A', in this case ACTG, in prefix table 300j is offset position 0. Accordingly, 'A' is associated with 0 in the offset table 300k. Similarly, the first lexeme starting with 'C', in this case CCGC, in prefix table 300j is in offset position 2. Accordingly, 'C' is associated with 2 in the offset table 300k. The process is repeated for nucleic acids 'G' and 'T'.

As with prefix counts offset tables are relatively inexpensive computer processing-wise to computer. Accordingly, an implementer may opt to pre-compute the offset table, or may opt to compute the offset table for every session where at least one search is to be performed.

Compressed PBWT Data Layout in Memory

As mentioned above, PBWT enables the amount of storage used to store the lexeme data to be greatly compressed. Consider a set of 1,000 genomic sequences, each having 100 base pairs denoted by a single nucleic acid. Since there are four nucleic acids, conceivably only 2 bits ($4=2^2$) need be used for each nucleic acid. Accordingly, 1,000 sequences× 100 nucleic acids per sequence×2 bits per nucleic acid=200, 000 bits. FIG. 4 provides an illustration 400 of compression in PBWT.

Consider the first row. For lexeme 402 CGC, it has a length 404 of 3, and a prefix 406 of C. All the preceding rows (not shown) had a prefix count 408 of 0 for A, C and T, and a prefix count 408 of 1 for G. Since the lexeme itself is not used in an existential search, the lexeme CGC need not be coded at all. The length may be coded in 7 bits (assuming that there never have a count greater than 128 ($128=2^7$). Here the length is 3, so the binary encoding is 0000011. As for coding the prefixes 402 associated with the lexeme 406, a bit mask can be created where a bit corresponds to each of the four nucleic acids, ACGT. Since in this example there are no prefixes of A, G and T, the $1^{st}$, $3^{rd}$ and $4^{th}$ positions are 0. But because there is a prefix of C, the $2^{nd}$ position is set to 1. Accordingly, the ACGT prefix bit map can be encoded in the four bits 0100.

Turning to the prefix counts, note that the prefix counts may be generated dynamically and therefore need not be coded. Consider the second row CTGC. Using the above techniques, it may be encoded as 0000100 (length 404) and 1000 (prefixes associated 406). After reading the first row CGC, in working memory, rather than in persistent memory, the PBWT routines will have stored a count of 1 prefix for G and 0 for A, C and T. Upon reading the C prefix for row CGC, it will increment, in working memory, the prefix count of C to 1. Thus, in working memory, the PBWT routines will store a count of 1 for prefixes C and G, and 0 for A and T. The key benefit is that persistent storage need not store the prefix counts, thereby saving memory in exchange for processing time. This technique of tracking counts may be referred to as a "rollup technique."

Note that the aforementioned rollup technique describes a pure tradeoff of storage (persistent) memory with respect to processing time. Prior art literature describe variations of rollups, for example with respect to FM Indexes and Burrows Wheeler Transforms (BWT). In some variations, a working bit may be added in storage to every nth record to aid in rollup.

However, in the aforementioned rollup technique, note that in storage, only 11 bits per record are used rather than 200 bits per record. Thus the 1,000 sequences only need 11,000 bits rather than the 200,000 bits in raw form, achieving a 94.5% compression in this example, without loss of accuracy.

Exemplary Operations on Data Transformed by the Prefix Burrows-Wheeler Transform Existence Searches, k-Mer Searches and Prefix Burrows-Wheeler Transform As previously mentioned, PBWT is optimized for existence searching. For example, in bioinformatics, the closed data domain is comprised of the four nucleic acids, adenine, cytosine, guanine and thymine, typically represented with their first letters A, C, G and T respectively. Data sets are typically sequences of these nucleic acids. A k-Mer is a permutation of these nucleic acids in the form of a sequence. A k-Mer search is an existence search for that particular k-Mer pattern in a data set.

Performing an Existence Search

Figure 5:
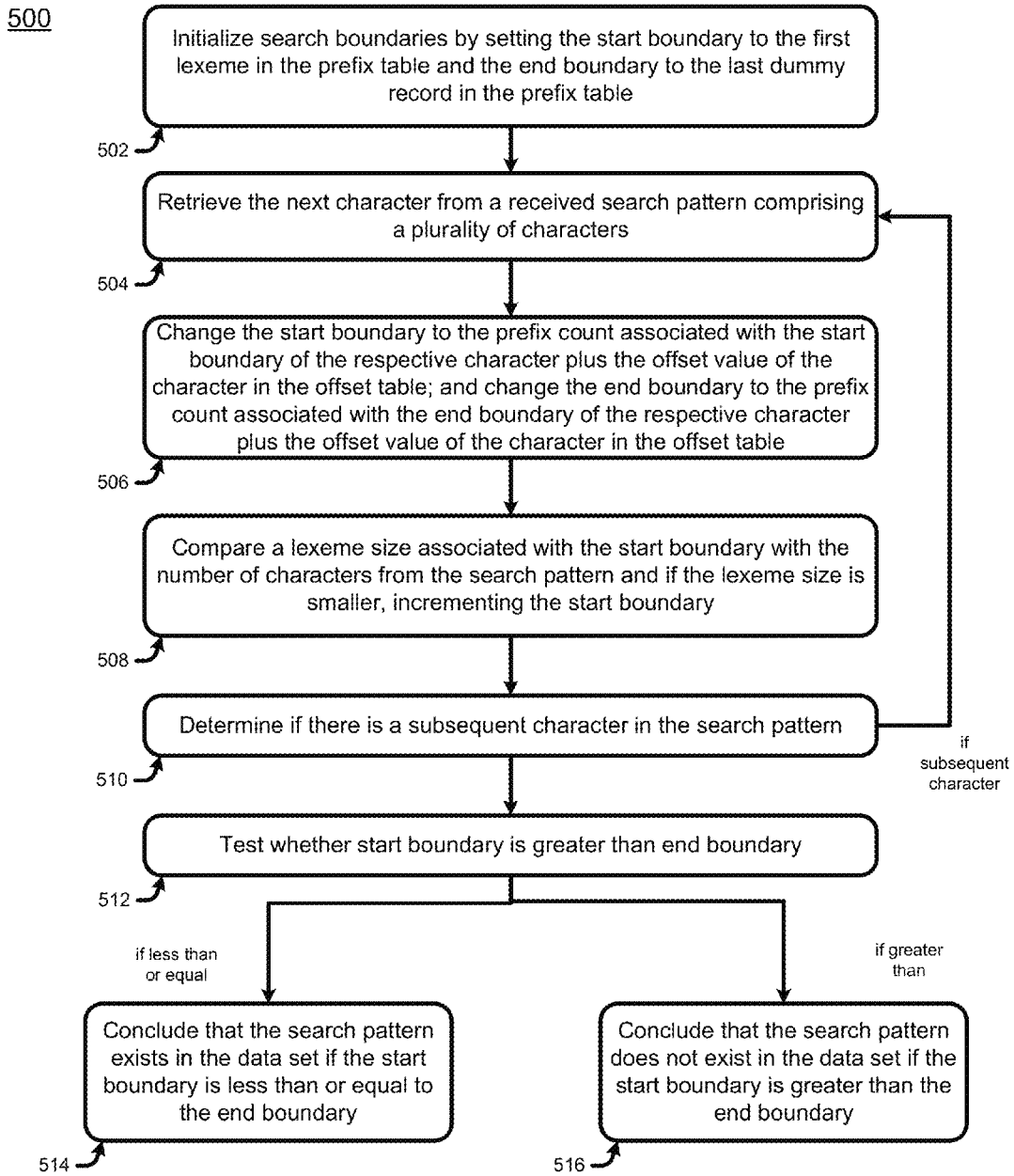
FIG. 5 is a flow chart of an exemplary k-Mer search data operation on data transformed by a Prefix Burrows-Wheeler Transform.

To perform an existence search, the prefix table, the prefix counts and the offset tables are computed in advance, either via preprocessing, or in the case of the prefix counts and offset tables, potentially interactively. FIG. 5 is a flow chart 500 of an exemplary existence search using PBWT, and FIGS. 6a through 6f illustrate different stages 600a-600f traversing the PBWT data, where the PBWT data has been prepared as with respect to FIGS. 1 and FIGS. 2a through 2k.

Initialization

A PBWT existence search starts with making a search boundary using the first and last records of the prefix table with a prefix count as the starting and ending boundaries respectively. Note that the last record is the dummy record while preparing the prefix counts in block 222 of FIG. 2. While iterating, the bounds are walked closer, and closer together, until it is determined that a search pattern is found, or otherwise that the search pattern does not exist in the data set.

The search boundary may be represented using the following notation: [X, Y) where X represents the start boundary, and Y represents one lexeme past the end of the data set, which is the ending boundary. Note that the square bracket denotes inclusion, and the closing parenthesis denotes exclusion, where Y is not necessarily a lexeme, and may be a dummy record.

Consider a search for GTGC in the prefix table in 600a of FIG. 6. In block 502 of FIG. 5, initialization is done by setting X to 0 and Y to 7.

Retrieve a Character from the Search Pattern and Modify the Search Boundary

To perform an existence search using PBWT, the search pattern is scanned from right to left. In block 504 of FIG. 5, a character is retrieved from the search pattern. Hence the first character to be retrieved from GTGC is the letter 'C.'

To modify the search boundaries, first the prefix counts associated with the search boundaries are looked up, as in block 506 of FIG. 5. For the start boundary X, note that in prefix table 600a of FIG. 6a, in row X (here 0), the prefix count for 'C' is 0. The offset corresponding to 'C' in the offset table (here 2) may be added, causing new start boundary of 2.

Similarly for the ending boundary Y, note that in prefix table 600a in FIG. 6a, in row Y (here 7), the prefix count for 'C' is 3. Again, the offset corresponding to 'C' in the offset table is 2. By adding, there is a new ending boundary of 5.

Thus the search boundary has been modified to [2, 5) as illustrated in prefix table 600b in FIG. 6b.

In decision block 508 of FIG. 5, the size associated with the starting boundary X is tested to see if it is greater than or equal to the size of the search pattern processed so far. In the example, the starting boundary X is 2, and the size associated with starting boundary X (at 2) is 4. Since only 'C' has been processed at this time, the size of the search pattern processed thus far is 1. Since 4>=1, processing is continued. If the size of the search pattern was larger, X would be incremented. This is a way of indicating that the search pattern being searched for existence, is larger than the lexeme, and therefore does not exist in the data set as will be seen in decision block 510 of FIG. 5.

If there is a subsequent character in the search pattern, as tested in block 510, processing continues back to block 504. Otherwise the results in block 512 are evaluated.

In decision block 512 of FIG. 5, whether X<Y is tested. If it is, the search pattern is determined to exist in the data set as in block 514. Otherwise, the search pattern does not exist in the data set as in block 516 and is accordingly reported.

To continue the example, the next character in GTGC is 'G'. So in block 504 of FIG. 5, 'G' is retrieved. As in block 506, at X=2, the prefix count for G is 0 and at Y=5, the prefix count for G is 1. The offset table is checked for 'G' and note that 5 should be added to both X and Y resulting in a new search boundary of [5, 6). This is illustrated in result 600c in FIG. 6c.

As in block 508 in FIG. 5, the size of the lexeme is checked to determine whether it is large enough to accommodate the search pattern thus far. Since the length of the search pattern thus far is 2 (i.e., the length of GC), the size associated with X (here 5) is 2, and 2>=2 it may be concluded that the lexeme can accommodate the search pattern thus far. Since there are additional characters in the search pattern to process, processing continues back to block 304.

Further continuing the example, in block 504 of FIG. 5 next character in GTGC is retrieved, in this case 'T'. As in block 506, at X=5, the prefix count for T is 0 and at Y=6, the prefix count for T is 1. The offset table is checked for for 'T' and based on the lookup 6 is added both to X and Y resulting in a new search boundary of [6, 7). This is illustrated this in result 600d in FIG. 6d.

As in block 508 of FIG. 5, the size of the lexeme is checked to determine whether it is large enough to accommodate the search pattern thus far. Since the length of the search pattern thus far is 3 (i.e., the length of TGC), the size associated with X (here 6) is 3, and 3>=3 it may then be concluded that the lexeme can accommodate the search pattern thus far. Since there are additional characters in the search pattern to process, processing continues back to block 504.

Processing the final character in this illustrative search pattern example, provides an illustration showing that a search string does not exist in a data set. In block 504 of FIG. 5, the next character is retrieved in GTGC which is 'G'. As in block 306, at X=6, the prefix count for G is 1 and at Y=7, the prefix count for T is 1. The offset table is checked for 'T' and note that 5 should be added both to X and Y resulting in a new search boundary of [6, 6). This is illustrated in result 600d in FIG. 6d.

As in block 508 of FIG. 5, the size of the lexeme is checked to see if it is large enough to accommodate the search pattern thus far. Since the length of the search pattern thus far is 4 (i.e., the length of GTGC), the size associated with X (here 6) is 3, which is less than 4, X is incremented by 1 per block 508. This results in a search boundary of [7, 6). Since X>Y, it may be concluded that the lexeme cannot accommodate the search pattern of GTCG and terminate processing. As in block 514, it may be reported that GTGC does not exist in the data set.

Note that the number of processing operations is linear with respect to the number of characters in the search pattern. This is because there is an iteration for every character in the search pattern. However, note that the time to search for the search pattern remains constant regardless of the size of the PBWT representation. Because the PBWT search relies on offsets, and because the offsets simply increase with the addition of new data, the time to search is independent of the size of the PBWT representation, thus regardless of the size of the database, the amount of time to search for a particular search pattern remains the same. Thus an advantage of PBWT is that performance will not suffer by adding more data, thereby lending itself to superior scalability.

Exemplary Merge Data Operations Using PBWT Techniques

Overview of Merge Operations

As mentioned above, upon receiving a plurality of datasets, one may search for a search pattern by separately searching the datasets. However, PBWT techniques provide the advantage of saving both space and processing operations. Therefore, it may be desirable to merge the plurality of datasets and then search the resulting merged dataset, since the merged dataset may take less working memory, without suffering loss of accuracy or data with respect to a desired data operation. Furthermore, the data operation will not suffer from a loss of processing efficiency.

For lexemes, the datasets are comprised of lexemes, and the data operation to be performed is an existential search for a lexeme. In one example, the lexemes may comprise genome sequence data and the existential search may be a search for a k-Mer.

Figure 7:
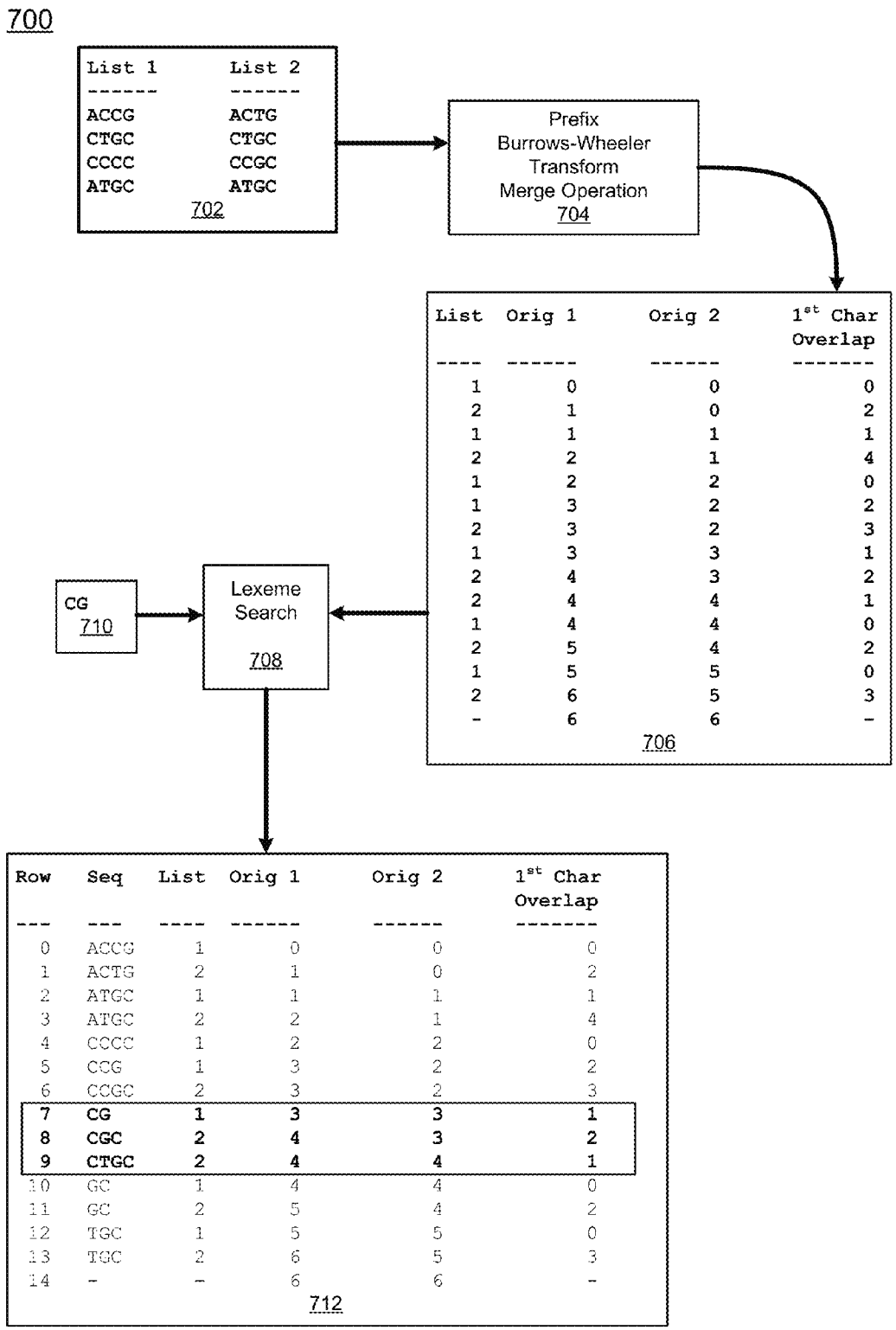
FIG. 7 is a top level diagram of creating and searching a merged lexeme set using Prefix Burrows-Wheeler Transform techniques.

Merge operations include creating a merged lexeme set from a plurality of lexeme sets and then performing an existential search on the resulting merged lexeme set. FIG. 7 is a top level illustration 700 of both creation and searching a merged lexeme set.

Specifically a first lexeme set and a second lexeme set 702 are received by a Prefix Burrows-Wheeler Transform Merge Operation 704. The Merge Operation 704 may comprise a receiving software module to receive the first lexeme set and the second lexeme set 702. The Merge Operation 704 may further comprise a merge table generation software module to generate a merged lexeme set 706 from the first lexeme set and the second lexeme set 702, where the merged lexeme set 706 retains information for each lexeme as to which of the first and second lexeme sets the lexeme originated. The process to generate a merged lexeme set 706 is described with respect to FIG. 8 and FIG. 9 below.

Once the merged lexeme set 706 is created, it may be searched. An existential search may be performed using a Lexeme Search 708. The Lexeme Search 708 may comprise a receiving software module configured to receive a search pattern in the form of a lexeme 710. The Lexeme Search 708 may further comprise a searching software module configured to perform an existence search (or other search), on the received search pattern 710.

An existential search may be performed using PBWT search techniques as described above with respect to FIG. 5 and FIG. 6 above. Upon receiving a range from applying a PBWT search technique, the merged lexeme set may be used as a lookup table to obtain the range in the original lexeme list, either the first lexeme list or the second lexeme list used to create the merged lexeme list. The process to perform an existence search on a merged lexeme set is shown with respect to FIG. 10 and FIG. 11 below.

Exemplary Process to Create a Merged Lexeme Set

Figure 8:
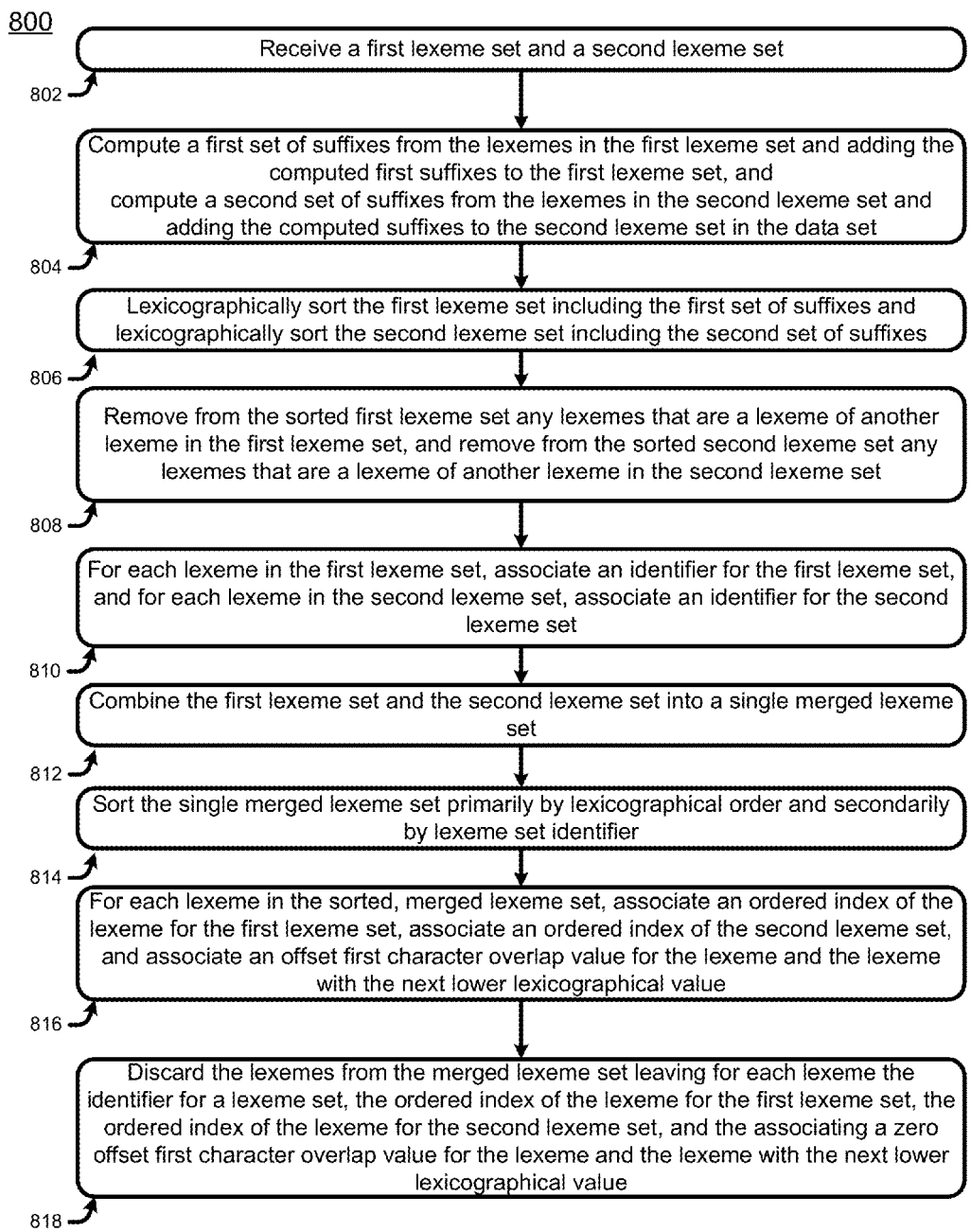
FIG. 8 is a flow chart of creating a merged lexeme set using Prefix Burrows-Wheeler Transform techniques.

FIG. 8 is a flow chart 800 of an exemplary process to create a merged lexeme set. FIGS. 9a through 9h illustrate the transformation of two received lists of lexemes to create a merged lexeme set. Although the data in the figures are that of genome sequence data, these techniques may be used without loss of generality on any lexeme set.

In block 802, a first lexeme set and a second lexeme set 900a of FIG. 9a are received. In block 804, the suffixes for all the lexemes in the first lexeme set and all the suffixes for the lexemes in the second lexeme set are generated and added to their respective lexeme sets. As shown in 900b of FIG. 9b, the suffixes for the first lexeme set are added to the first lexeme set and the suffixes of the second lexeme set are added to the second lexeme set.

In block 806, as shown in 900c of FIG. 9c, the first lexeme set with the added respective suffixes is lexicographically sorted, and the second lexeme set with the added respective suffixes is lexicographically sorted.

In block 808, as shown in 900d of FIG. 9d, all lexemes in the first lexeme set that are prefixes of a lexeme in the first lexeme set, and all lexemes in the second lexeme set that are prefixes of a lexeme in the second lexeme set are removed. Note that, as with other PBWT techniques previously discussed above, the removal of the prefixes may be performed linearly, by scanning the respective lists from the lowest lexicographical value, to the highest, where if a lexeme as a prefix of the lexeme with the next highest lexicographical value, it is removed. In this way prefixes may be efficiently removed.

In block 810, as shown in 900e of FIG. 9e, each lexeme in the first lexeme set is associated with an identifier of the first lexeme set. Here that identifier is "1." Similarly, each lexeme in the second lexeme set is associated with an identifier of the second lexeme set. Here that identifier is "2." These identifiers will be later used, to preserve the information as to which list a lexeme came from. These identifiers may be also called "origin identifiers" since they identify the list where a lexeme "originated" or came from.

In block 812, the first lexeme set and the second lexeme set is merged together. In block 814, the merged first lexeme set and second lexeme set are then sorted by lexeme and then by lexeme set identifier. As shown in the merged lexeme set 900f of FIG. 9f, for example note that the lexeme "GC" is in both the first lexeme set identified with "1" and the second lexeme set identified with "2." Accordingly, the two "GC" records are sorted with the first lexeme set identifier first, and the second lexeme set identifier second.

In block 816, three numbers are associated with each lexeme: (i) the index of the lexeme with respect to the first lexeme set (Origin Index for Set 1), (ii) the index of the lexeme with respect to the second lexeme list (Origin Index for Set 2), and (iii) the offset of the first character overlap.

To generate the Origin Index for Set 1, identify the zero based indexes for lexeme set 1. Referring to 900e in FIG. 9e, note that the following indices may be associated with set 1 as follows:

0 ACCG
1 ATGC
2 CCCC
3 CCG
4 CG
5 GC
6 TGC

For each lexeme associated with the first lexeme set, as denoted with the first lexeme set identifier of "1", is then associated with the corresponding index.

A dummy record storing the last index (in this case 6) is then provided, for the Origin Index.

However, the lexemes with a second lexeme set identifier of "2", there is no Origin Index for Set 1. The lexemes with a second lexeme set identifier of "2" are then subsequently associated with an Origin Index of the smallest Origin Index that comes after the lexeme. For example, ATGC for set 2, the smallest Origin Index for all lexemes afterwards is 2, from CCCC. Therefore, ATGC will receive an Origin Index for Set 1 of value 2. Similarly, for CGC for set 2 and CTCG for set 2, the smallest Origin Index for all lexemes afterwards is 4. Therefore, both CGC for set 2 and CTCG for set 2 will both receive an Origin Index for Set 1 of value 4.

The Origin Index for Set 2 may be performed in the same way for Set 1, except starting with the zero offset index for the second lexeme set, and backfilling the Origin Indexes for lexemes from set 1.

The first character overlap is the place, from left to right where there is a character overlap between a lexeme, and the lexeme that immediate precedes it in lexicographical order.

For example, in 900g of FIG. 9g, ACCG does not have any preceding lexeme. Therefore, the first character overlap is set to 0. However, ACTG has overlap in the first two characters AC. So the first character overlap is set to 2. In the case of ATCG and ATCG, which are identical, the first character overlap is 4, representing all four characters being identical. The result of the association of the Origin Indexes and the first character overlap values is shown in 900g of FIG. 9g.

Item 900g of FIG. 9g may be considered a PBWT merge table. However, as with an ordinary PBWT prefix table, it is not necessary to store the lexemes themselves. Accordingly, to save memory, the lexemes may be deleted. The result is a PBWT merge table 900h of FIG. 9h. For nomenclature purposes, 900g of FIG. 9g may be referred to as a lexeme added PBWT merge table and 900h of FIG. 9h may be referred to as a lexeme deleted PBWT merge table.

Exemplary Process to Search a Merged Lexeme Set

Figure 10:
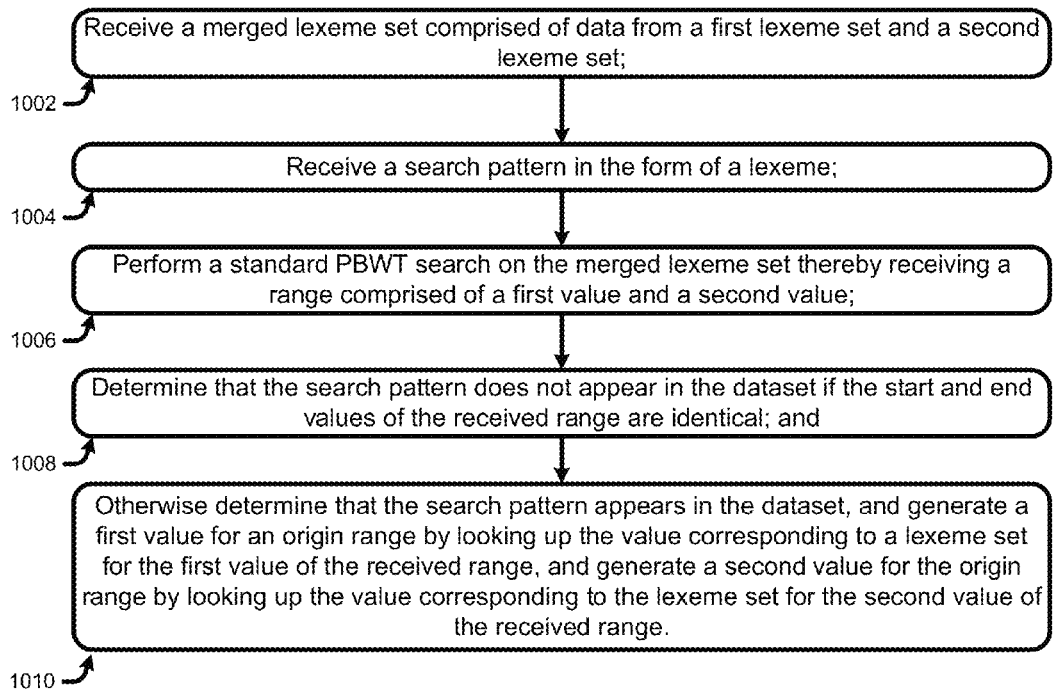
FIG. 10 is a flow chart of searching a merged lexeme set using Prefix Burrows-Wheeler Transform techniques.

Upon creation of a PBWT merge table, one may perform existential searches on the PBWT merge table. FIG. 10 is a flow chart 1000 to perform an existential search. FIG. 11 is an example PBWT merge table (or more generically a merged lexeme set) 1100 in the process of being used for an existential search, in this case for the lexeme "CG."

In block 1002, of FIG. 10, a merged lexeme set 1100 of FIG. 11 is received, that has been generated from data from a first lexeme set and a second lexeme set. Here, the merged lexeme set 1100 corresponds to 900h from FIG. 9h.

In block 1004, of FIG. 10, a search pattern is received, here the lexeme "CG." A standard PBWT existence search is then performed in block 1006 as shown with respect to FIG. 5 and FIG. 6 above. As shown in 1100 of FIG. 11, a range of [7, 9) is received as illustrated with the boxed records of "CG", "CGC", and "CTGC". Note that the parenthesis denotation of 9 of the range [7, 9) indicates that the 9$^{th}$ record does not actually belong to the set. The inclusion of record 9 in the box is to help illustrate using 1100 of FIG. 11 as a lookup table.

In block 1008, if the start and end values of the range are identical, it may then be concluded that "CG" is not in the PBWT merge table. In block 1010, if the start and end values of the range are not identical, it may then be concluded that "CG" is in the PBWT merge table. Note that the first value is 7 and the second value is 9. Since 7 does not equal 9, it may then be concluded per block 1010 that "CG" is indeed in the PBWT merge table.

The corresponding range is then identified in one of the original lexeme sets. For example, to determine the corresponding range in the second lexeme set, which has Origin Indexes for Set 2, the corresponding value in the merge table 1100 of FIG. 11 need only be found. Here, for [7, 9), the Origin Index for Set 2 for record 7, is 3. Similarly, for [7, 9) the Origin Index for Set 2 for record 9, is 4. Accordingly, for range [7, 9) returned from a PBWT existential search, the range for the second lexeme set is [3, 4).

Thus a merge operation with the benefits of compression using PBWT techniques on merged datasets without losing the information of the indexes of the original lexeme sets is disclosed above.

Exemplary Hardware, Software and Communications Environment

Computing Device

Figure 12:
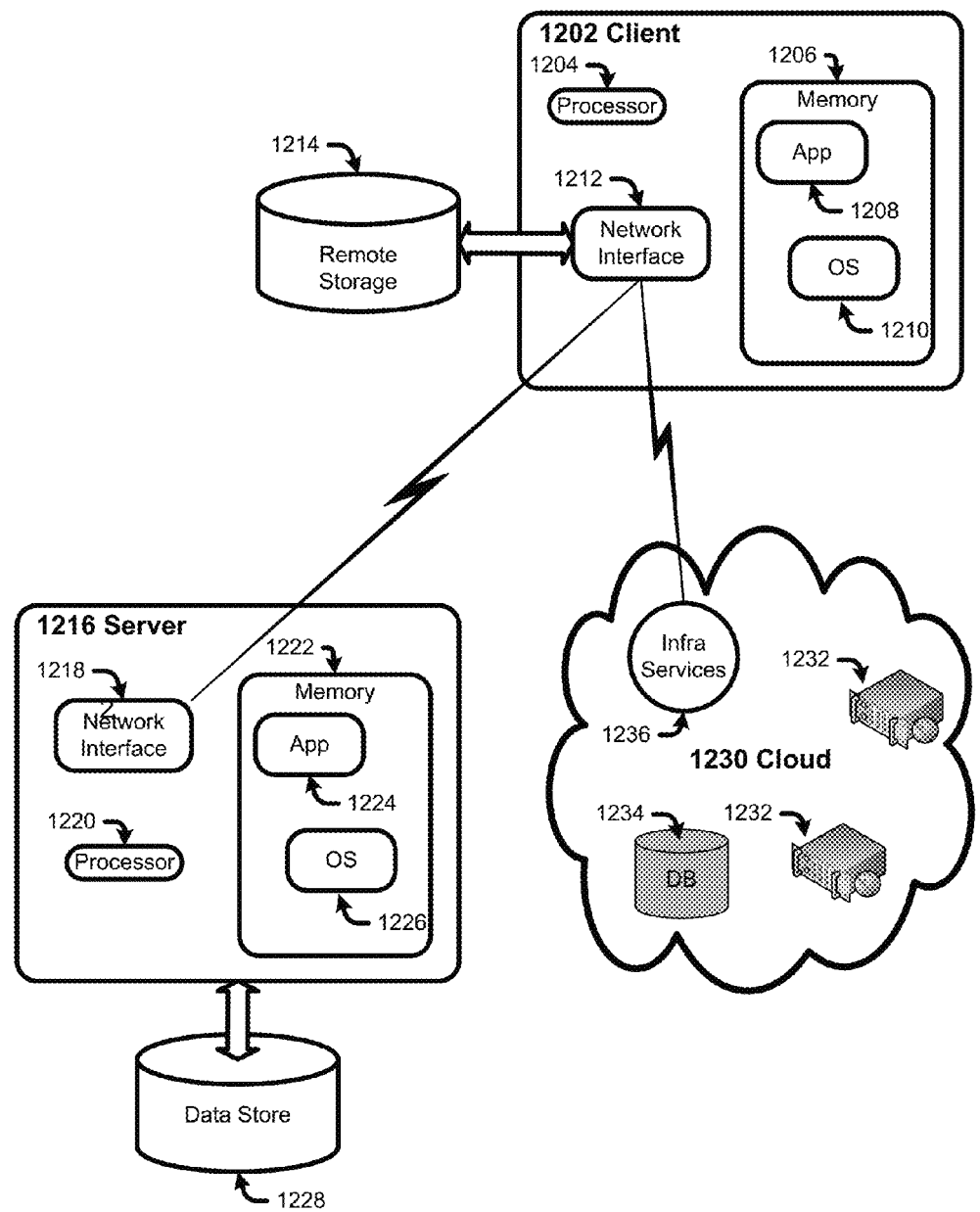
FIG. 12 is a diagram of an exemplary hardware, software and communications environment for a Prefix Burrows-Wheeler Transform.

FIG. 12 illustrates several possible embodiments of a hardware, software and communications environment 1200 for PBWT techniques.

Client device 1202 is any computing device. Exemplary computing devices include without limitation personal computers, tablet computers, smart phones, and smart televisions and/or media players.

PBWT techniques have the advantage of being very compact and very efficient with processing. Although PBWT techniques may be brought to bear on a typical networked client device 1202 accessing a remote server, PBWT may be realistically implemented on a standalone computer. Accordingly, PBWT might be on a client device 1202 that is a portable laptop, or a portable embedded system, or a standalone stations such as a kiosk. For example, a researcher in the field may have a custom computing device that contains an integrated computer running PBWT. Alternatively, a research lab may have an enclosed station that also contains an integrated computer running PBWT.

A client device 1202 may have a processor 1204 and a memory 1206. Client device 1202's memory 1206 is any computer-readable media which may store several software components including an application 1208 and/or an operating system 1210. In general, a software component is a set of computer executable instructions stored together as a discrete whole. Examples of software components include binary executables such as static libraries, dynamically linked libraries, and executable programs. Other examples of software components include interpreted executables that are executed on a run time such as servlets, applets, p-Code binaries, and Java binaries. Software components may run in kernel mode and/or user mode.

Computer-readable media includes, at least, two types of computer-readable media, namely computer storage media and communications media. Computer storage media includes volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transmission mechanism. As defined herein, computer storage media does not include communication media.

To participate in a communications environment, user equipment device 1202 may have a network interface 1212. The network interface 1212 may be one or more network interfaces including Ethernet, Wi-Fi, or any number of other physical and data link standard interfaces. In the case where the user need only do operations on a standalone single machine, the network interface 1212 is optional.

Client-Server/Multi-Tier

Client 1202 may communicate to a server 1216. Server 1216 is any computing device that may participate in a network. The network may be, without limitation, a local area network ("LAN"), a virtual private network ("VPN"), a cellular network, or the Internet. The client network interface 1212 may ultimate connect remote networked storage 1214, or to server 1216 via server network interface 1218. Server network interface 1218 may be one or more network interfaces as described with respect to client network interface 1212.

Server 1216 also has a processor 1220 and memory 1222. As per the preceding discussion regarding client device 1202, memory 1222 is any computer-readable media including both computer storage media and communication media.

In particular, memory 1222 stores software which may include an application 1224 and/or an operating system 1226. Memory 1218 may also store applications 1224 that may include without limitation, an application server and a database management system. In this way, client device 1202 may be configured with an application server and data management system to support a multi-tier configuration.

Server 1216 may include a data store 1228 accessed by the data management system. The data store 1228 may be configured as a relational database, an object-oriented database, a NoSQL database, and/or a columnar database, or any configuration to support scalable persistence.

Cloud

The server 1216 need not be on site or operated by the client enterprise. The server 1216 may be hosted in the Internet on a cloud installation 1230. The cloud installation 1230 may represent a plurality of disaggregated servers which provide virtual web application server 1232 functionality and virtual database 1234 functionality. Cloud 1230 services 1232, 1234 may be made accessible via cloud infrastructure 1236. Cloud infrastructure 1236 not only provides access to cloud services 1232, 1234 but also billing services. Cloud infrastructure 1236 may provide additional service abstractions such as Platform as a Service ("PAAS"), Infrastructure as a Service ("IAAS"), and Software as a Service ("SAAS").

Applications of Prefix Burrows-Wright Transform

Common Contexts of PWBT Applications

PBWT techniques may be advantageously applied to large data sets with an ordered character set, where the character set is finite, and where search data operations show the existence of an instance of the item to be search in the data set, rather than the specific location.

The specification of an ordered and finite character set is a result of the PBWT relationships to string searching techniques. However non-string data may be encoded to a finite, ordered character set, and PBWT techniques applied to the encoding. For example, signal wave data from a cellular phone may be sampled, amplitudes encoded into strings, and the results encoded strings searched with PBWT. Such a technique could be used to detect patterns of power/transmission loss in cell phones.

PBWT techniques are lossless in the sense that the information content itself is not lost. However, PBWT techniques may be considered lossy in the sense that the location of a substring may be lost. Accordingly, PBWT has strong applicability in scenarios searching for an existence of an instance rather than location. For example, PBWT may be able to determine that there is an error in a cellular transmission, but it may not be able to determine where in the data set the error occurred. Examples of such scenarios are as follows.

Plagiarism Searches

Plagiarism is the passing off of another author's works as one's own. Ordinarily, portions of another author's works are generally marked with citations. Copyrighted material is usually associated with copyright notices, where permission from the original author or the author's agents have been obtained. However, with plagiarism, the plagiarist misappropriates the credit for another author's expressions.

Plagiarism exists in both professional and academic publishing circles. Detecting plagiarism is a difficult due to the large amount of material that may be plagiarized. Accordingly, plagiarism detection is a candidate for automation.

Plagiarism detection may make use of PBWT techniques by selecting passages suspected of plagiarism as a search pattern. A corpus of known literature of the field is then processed into PBWT and the selected passage searched for. If there is a match, then it is likely that plagiarism has been detected.

Although PBWT performs exact matches, thus paraphrased plagiarism might not be detected, PBWT has the advantage of being fast, portable due to its compression, and able to compare against a much larger corpus of known literature.

Open Source Clearance

Open source clearance relates to companies ensuring that their proprietary software does not contain open source. Often developers may copy source code from the internet and other sources without being aware that the source code was subject to an open source license. Since many open source licenses oblige the surrender of intellectual property rights, such additions may result in code intended to be proprietary losing those intellectual property rights. This phenomenon is known as "tainting."

An open source clearance is a due diligence search by a company, prior to releasing proprietary source code to detect whether any open source had been added. PBWT techniques may be brought to bear by setting a suspect code snippets against a corpus of open source code compressed into a PBWT prefix table and offset table.

As with a plagiarism detector, PBWT will not detect paraphrased or modified source code. However, it will detect simple cut and pasted source code and will have the advantage of being able to perform comparisons against a very large corpus of source code known to be from open source repositories.

Bioinformatics Specific Applications of Prefix Burrows-Wright Transform

Genome Assembly

PBWT techniques are particularly useful in the context of high speed DNA sequencing. DNA sequencing involves reading short sequences, called "reads", that are a portion of a genome, and then re-assembling the reads into the original genome. DNA sequencing generally may be performed via one of two strategies. One strategy is in mapping sequencing, where the reads are mapped to an existing backbone genome structure, akin to mapping details of the genome to an outline of the genome. Another strategy is in de-novo genome assembly, where reads are assembled by matching one read to another via searching for predetermined sequences. De-novo genome assembly derives its name from the possibility of the resulting sequences being novel sequences.

In both mapping and de-novo sequencing, consider a read to be matched to a location on a backbone or to another read respectively. PBWT techniques may be used in a k-Mer search to locate the backbone location in the case of mapping sequencing and for another read in the case of de-novo assembly. For example, in the case of de-novo assembly, all the reads may be stored in memory in PBWT format. A read to be matched to another read has a k-Mer identified to be used as a search pattern. The identified k-Mer is usually a known overlap between reads. This predetermined overlap k-Mer is then searched on all the reads stored in memory using a PBWT k-Mer search, thereby identifying whether a match exists or not. Accordingly, this information may be used in the construction of graph data structures, such as read overlap graphs and de Bruijn graphs, representing possible overlaps used to reconstruct the genome.

In the case of de-novo assembly, typically a large number of reads are matched to other reads. Since the PBWT format is merely being searched, rather than modified, matching of multiple reads may be performed in parallel. Accordingly, a dispatcher using parallel techniques, such as map-reduce, may spawns parallel read match operations thereby considerably speeding de-novo sequencing.

Searching for Genomic Defect

Another example of applying PBWT techniques in bioinformatics is in searching for a genome defect. Consider the case of a researcher who suspects that a particular genetic sequence of nucleic acids is a marker for a particular birth defect. The researcher may then set that particular genetic sequence as the search pattern and then perform a k-Mer search on a person under study. If the sequence is detected, it could then be correlated with the incidence or the absence of the birth defect in the person under study.

It is worth observing that there are other ways to perform a k-Mer search. However, the advent of PBWT techniques enables the processing to be performed in a short number of days rather than several months. Accordingly, PBWT techniques provide several factors of improvement in processing speed hitherto not available with prior art techniques.

Searching for Plant Tags

Another potential bioinformatics application of PBWT techniques is to search for biological tags in plants. Governments may seek to track the source of botanical plants. For example, some plants may be genetically modified and subject to certain regulations. By way of another example, some states have legalized marijuana and may wish to track plant sources a part of regulation. One way to track plants is to add a genetic tag to the plants to be tracked. Later, if a regulator or law enforcement officer confiscates some plants, they may be rapidly analyzed using PBWT. Specifically the biological tag, in the form of a k-Mer, is set as the search pattern. Using a PBWT k-Mer search, one may identify the tag, or the absence of a genetic tag in a plant. Accordingly, the source of the plant, or the contraband source of a plant could be readily identified.

Again, it is worth observing that the speed and efficiency of PBWT makes such a scenario possible. Using prior art methods, the slowness of processing would create a massive backlog of genetic tag searches as to render the process impractical. However, with PBWT, the compressed data is easily stored even in an embedded system, and the amount of time to perform the k-Mer search is sufficiently small as to render genetic tagging practical as a regulatory tool.

CONCLUSION

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:
   receiving a first lexeme set and a second lexeme set;
   computing a first set of suffixes from first lexemes in the first lexeme set, and a second set of suffixes from second lexemes in the second lexeme set;
   adding the first set of suffixes to the first lexeme set, and the second set of suffixes to the second lexeme set;
   sorting, in an ascending lexicographical order, the first lexeme set to create a first sorted lexeme set and the second lexeme set to create a second sorted lexeme set;
   determining whether at least two of the first lexemes in the first sorted lexeme set are identical;
   removing the at least two of the first lexemes from the first sorted lexeme set in response to determining that the at least two of the first lexemes are identical
   associating a first lexeme set identifier with each of the first lexemes within the first sorted lexeme set, and a second lexeme set identifier with each of the second lexemes within the second sorted lexeme set;
   combining the first sorted lexeme set and the second sorted lexeme set to create a single merged lexeme set;
   sorting the single merged lexeme set primarily by lexicographical order and secondarily by the first lexeme set identifier and the second lexeme set identifier; and
   associating, within the single merged lexeme set, a first origin index value with individual first lexemes of the first lexeme set and a second origin index value with individual second lexemes, of the second lexeme set, the first origin index value indicating a lexicographical position of the individual first lexemes within the first lexeme set, and the second origin index value indicating a second lexicographical position of the individual second lexemes within the second lexeme set; and
   associating individual offset first character overlap values to the individual first lexemes and the individual second lexemes within the single merged lexeme set, the individual offset first character overlap values corresponding to a number of first characters of a particular lexeme that are identical to first characters of a preceding lexeme.

2. The method of claim 1, comprising:
   discarding the first lexemes and the second lexemes from the single merged lexeme set.

3. The method of claim 1, further comprising:
   comparing, within the first lexeme set, a particular lexeme of the first lexemes at a particular lexicographical value with a next lexeme of the first lexemes at a next highest lexicographical value; and
   removing the particular lexeme from the first lexeme set, based at least in part on the particular lexeme being a prefix of the next lexeme.

4. The method of claim 1, wherein the first lexemes of the first lexeme set and the second lexemes of the second lexeme set are genome sequence data.

5. The method of claim 1, further comprising:
determining that at least two of the second lexemes in the second sorted lexeme set are individual; and
removing the at least two of the second lexemes from the second sorted lexeme set.

6. A system to create a merged lexeme set from a plurality of lexeme sets, suitable for performing an existential search of lexemes, comprising:
a processor;
a memory communicatively coupled to the processor;
a receiver software component stored in the memory configured to receive a first lexeme set and a second lexeme set; and
a merged lexeme set generator stored in the memory configured to generate a merged lexeme set from the first lexeme set and the second lexeme set received by the receiver software component, the merged lexeme set including at least a first origin index value for individual first lexemes of the first lexeme set and a second origin index value for individual second lexemes of the second lexeme set, wherein an existential lexeme search is based at least in part on the first lexeme set and the second lexeme set within the merged lexeme set, and wherein information in the merged lexeme set includes at least a subset of information from the first lexeme set and the second lexeme set.

7. The system of claim 6, wherein the subset of information includes at least the first origin index value for the individual first lexemes of the first lexeme set and the second origin index value for individual second lexemes of the second lexeme set, and omits the first lexemes and the second lexemes.

8. The system of claim 6, comprising a persistent memory communicatively coupled to the memory and the processor, configured to store a lexeme set generated by the merged lexeme set generator.

9. The system of claim 6, wherein the first lexeme set and the second lexeme set include genome sequence data.

10. The system of claim 6, wherein the process is a first processor, the system further comprising a network interface and a remote processor communicatively coupled to the first processor via the network interface and wherein at least some of the processing is performed on the remote processor.

11. The system of claim 10, wherein the processor is accessed via Internet protocols.

12. The system of claim 10, wherein the remote processor is on a server in a cloud data center.

13. The system of claim 6, wherein the system is hosted on a platform capable using parallel processing techniques.

14. The system of claim 6, wherein the processor, memory and data store are combined into a single standalone embedded system.

15. A method to perform an existential search for a lexeme in a merged lexeme set, comprising:
receiving a search pattern as a lexeme;
performing a standard Prefix Burrows-Wheeler Transform (PBWT) search on a merged lexeme set, the merged lexeme set including a first lexeme set and a second lexeme set, wherein individual lexemes within the merged lexeme include a prefix count that indicates a lexicographical order of the individual lexemes within the merged lexeme set;
determining a search boundary from the merged lexeme set, based at least in part on a a first lexeme value and a second lexeme value, the first lexeme value corresponding to a starting lexicographical position for the search boundary, and the second lexeme value corresponding to an ending lexicographical position for the search boundary;
determining that the search pattern does not match a lexeme value within the search boundary; and
identifying a first character from the search pattern, the first character being a most-right character of the search pattern;
identifying a particular lexeme within the search boundary with a prefix that matches the first character from the search pattern; and
generating a modified first lexeme value to create a modified search boundary, based at least in part on an offset value associated with the particular lexeme, the offset value corresponding to a lexicographical position of the particular lexeme.

16. The method of claim 15, wherein the first lexeme set and the second lexeme set include genome sequence data, and the existential search is a k-Mer search.

17. A system to perform an existential search for a lexeme in a lexeme merge table, comprising:
a processor;
a memory communicatively coupled to the processor;
a persistent memory communicatively coupled to the memory and the processor, configured to store a merged lexeme set comprising data from a first lexeme set and from a second lexeme set;
a receiver software component stored in the memory configured to receive at least one lexeme upon which to perform an existential search on the merged lexeme set stored in the persistent memory; and
an existential search software component stored in the memory configured to perform an existential search on the merged lexeme set stored in the persistent memory, wherein the existential search is based at least in part on the first lexeme set and the second lexeme set within the merged lexeme set, and wherein the merged lexeme set includes at least a subset of information from the first lexeme set and the second lexeme set.

18. The system of claim 17, wherein the the subset of information includes at least a first origin index value for individual first lexemes of the first lexeme set and a second origin index value for individual second lexemes of the second lexeme set, the subset of information further omitting the individual first lexemes and the individual second lexemes.

19. The system of claim 17, wherein the first lexeme set and the second lexeme set include genome sequence data, and the existential search is a k-Mer search.

20. The system of claim 17, wherein the processor is a first processor, the system further comprising a network interface and a remote processor communicatively coupled to the first processor via the network interface and wherein at least some of the processing is performed on the remote processor.

21. The system of claim 20, wherein the processor is accessed via Internet protocols.

22. The system of claim 21, wherein the remote processor is on a server in a cloud data center.

23. The system of claim 17, wherein the system is hosted on a platform capable using parallel processing techniques.

24. The system of claim 17, wherein the processor, memory and data store are combined into a single standalone embedded system.

25. The system of claim 17, further comprising a co-processor communicatively coupled to the processor and to the memory, wherein the co-processor is specific to performing an existential search on a merge table, and wherein a least some of the processing is performed on the co-processor.

\* \* \* \* \*